United States Patent [19]
Yu et al.

[11] Patent Number: 5,695,970
[45] Date of Patent: Dec. 9, 1997

[54] GLUCAN LYASE PRODUCING 1,5-ANHYDROFRUCTOSE

[75] Inventors: Shukun Yu, Malmö ; Marianne Pedersen, Rallarvägen; Lennart Kenne, Märsta, all of Sweden

[73] Assignee: T&M Biopolymer Aktiebolag, Uppsala, Sweden

[21] Appl. No.: 416,709

[22] PCT Filed: Oct. 19, 1993

[86] PCT No.: PCT/SE93/00854

§ 371 Date: Apr. 18, 1995

§ 102(e) Date: Apr. 18, 1995

[87] PCT Pub. No.: WO94/09122

PCT Pub. Date: Apr. 28, 1994

[30] Foreign Application Priority Data

Oct. 21, 1992 [SE] Sweden .................................. 9203084

[51] Int. Cl.$^6$ .............................. C12P 19/02; C12N 9/88; C12N 1/20
[52] U.S. Cl. .................... 435/105; 435/232; 435/252.33; 435/252.3; 435/257.2; 536/23.2
[58] Field of Search ................... 435/232, 257.1, 435/105, 257.2; 536/23.2

[56] References Cited

PUBLICATIONS

Yu et al. "alpha–1,4 Glucan lyase, a new class . . . I. Efficient purification and characterization from red seaweeds" Biochimica et biophysica Acta 1156, 313–320, Mar. 1993.
Yu et al. "alpha–1,4 Glucan lyase, a new class, . . . II. Subcellular localization and partial amino–acid sequence." Planta 191, 137–142, 1993.
Baute et al. "Fungal bioconversions yielding unusual antibiotic pyrones from carbohydrates. XV–Biogenesis . . . " Bull. Soc. Pharm. Bordeaux 128, 9–18, 1989.
Phytochemistry, vol. 27, No. 11, 1988, M–A Baute et al, "Fungal enzymatic activity degrading 1,4–alfa–D–glucan to 1,5–D–anhydrofructose" pp. 3401–3403.
Dialog Information Services, file 154, Medline, Dialog acc.No. 05922849, Nakamura T. et al: "Oxidation of 1,5–anhydro–D–glucitol to 1,5–anhydro–D–fructose catalyzed by an enzyme from bacterial membranes", J. Biochem (Tokyo) Mar. 1986, 99 (3) pp. 607–613.
Phytochemistry, vol. 30, No. 5, 1991, M–A Baute et al, "Fungal enzymatic activity degrading 1, 4–alfa–D–glucans to echinosporin (5–epipentenomycin I)" pp. 1419–1423.

*Primary Examiner*—Robert A. Wax
*Assistant Examiner*—Nashaat T. Nashed
*Attorney, Agent, or Firm*—Bacon & Thomas

[57] ABSTRACT

The invention relates to an enzyme, exo-α-1,4-glucan lyase, capable of successively cleaving the terminal α-1,4-D-glucosidic bonds from the non-reducing ends of an α-1,4-glucan. The enzyme is selected from the group consisting of α-1,4-glucan lyase isolated from an alga and functional derivatives and analogs derived from a nucleotide sequence related to an alga α-1,4-glucan lyase. Further, a method of enzymatically cleaving the terminal α-1,4-D-glucosidic bonds from the non-reducing ends of an α-1,4-glucan, and the degradation product 1,5-anhydrofructose for use as an oxygen radical scavenger or anti-oxidant and/or as a sugar substitute, are disclosed. Additionally, a method of producing an enzyme capable of successively cleaving the terminal α-1,4-glucosidic bonds from the non-reducing ends of an α-1,4-glucan; an antibody which binds to the amino acid sequence of the enzyme, and a DNA or RNA probe which recognizes a nucleotide sequence coding for the enzyme, are described.

12 Claims, No Drawings

GLUCAN LYASE PRODUCING 1,5-ANHYDROFRUCTOSE

This is the national stage application of PCT/SE93/00854, filed Oct. 19, 1993.

The present invention relates to a new enzyme and applications thereof. More precisely, it relates to an enzyme, exo-α-1,4-glucan lyase, which is capable of successively cleaving the terminal α-1,4-D-glucosidic bonds from the non-reducing ends of an α-1,4-glucan and a method of producing the same. The main degradation product is 1,5-anhydrofructose. It has now been shown that 1,5-anhydrofructose is useful as an oxygen radical scavenger or an anti-oxidant and as a substitute for other sugars and their derivatives.

BACKGROUND

It is well known that the degradation of α-glucans (maltosaccharides, starches and glycogen) is catalyzed by two groups of enzymes, hydrolases and phosphorylases, yielding the degradation products glucose and glucose 1-phosphate. In studying metabolites in algae a new enzyme that can degrade α-glucans was suprisingly found. Research efforts resulted in characterization of the enzyme and the finding that the enzyme degrades starch yielding one major product which was analyzed to be 1,5-anhydrofructose.

The compound 1,5-anhydrofructose (AF) was first synthesized chemically by Lichtenthaler F. W., et al in 1980 (Tetrahedron Letters Vol. 21, pp. 1429–1432). It was proposed to be useful in the synthesis of other 1,5-anhydroketoses. Baute M-A., et al (Phytochemistry, Vol. 27, No. 11, pp. 3401–3403, 1988) reported that a crude preparation of an enzyme activity from fungi could degrade starch to AF. Their pure AF could be prepared from starch in 40–50 % yield by removing glucose with baker yeast and maltose by gel filtration. The enzyme was not purified and the authors disclosed that the fungi that had been tested possesses an enzyme (or an enzyme system), and they disclose in the discussion part that the presence of glucose and maltose among the products of the reaction might result either from minor activity of the enzyme or from its contamination by one or several conventional amylolytic enzymes. Further, Baute, M-A. et al (Phytochemistry 1987, 26 (5), 1391-3 and 1991, 30 (5), 1419-25, respectively) disclosed that their enzymic activity degrades 1,4-α-D-glucans to 1,5-D-anhydrofructose and then converts this sugar to the antibiotics microthecin and pentenomycin.

There is no disclosure in the prior art that 1,5-anhydrofructose would be an oxygen radical scavenger or anti-oxidant and as a substitute for other sugars and their derivatives.

DESCRIPTION OF THE INVENTION

The new enzyme, exo-α-1,4-glucan lyase, can be obtained from algae, specifically red algae of the order of Gigartinales. Such an enzyme, having a molecular weight of approximately 54 000 Da, has been obtained from *Phyllophora truncata*. However, the experiments disclosed in this specification was conducted with such an enzyme which was isolated from the two red seaweeds *Gracilariopsis lemaneiformis* and *Gracilaria verrucosa*. The reaction catalyzed is cleavage of the terminal α-1,4-D-glucosidic bonds of an α-1,4-glucan successively from the non-reducing ends of the chains with the formation of 1,5-anhydrofructose.

1. When a linear α-1,4-glucan, such as maltose, maltosaccharides and amylose, is used as a substrate:

$$\text{Linear } \alpha\text{-glucan} \rightarrow \text{AF+Glucose} \quad \quad 1)$$

The products are AF and glucose. The yield of AF $(\%)=(n-1)/n \times 100$. The yield of glucose $(\%)=1/n \times 100$. n indicates the polymerization number of this α-glucan. For example, if the glucan has 100 glucose units, the yield of AF is 99%, while the yield of glucose is 1%.

2. When a branched glucan (α-1,4-glucan with α-1,6-branches), such as amylopectin and glycogen, is used as a substrate $$\text{Branched glucan} \rightarrow \text{AF+neo-limit dextrin} \quad \quad 2)$$

The products are AF and a neo-limit dextrin. The enzyme will release AF from the non-reducing ends and the degradation stops when a α-1,6-linked glucose unit is met. Therefore the yield of AF depends on the chain length with non-reducing ends in the whole α-glucan molecule.

The proposed naming of this enzyme is: Exo-α-1,4-glucan lyase; α-1,4-glucan 1,5-anhydrofructose eliminase; α-1,4-glucan exolyase; systematic name: α-1,4-glucan exo-4-lyase (1,5-anhydrofructose-forming), (EC 4.2.2. X )

The proposed naming of this enzyme is according to rules set by the Enzyme Commission of the International Union of Biochemistry. The number X will be numbered by the Commission after an application.

Thus, one aspect of the invention is directed to an enzyme, exo-α-1,4-glucan lyase, capable of successively cleaving the terminal α-1,4-D-glucosidic bonds from the non-reducing ends of an α-1,4-glucan. In a preferred embodiment of this aspect of the invention said enzyme is selected from the group consisting of α-1,4-glucan lyase isolated from an alga and functional derivatives and analogs derived from a nucleotide sequence related to an algal α-1,4-glucan lyase.

In a specific embodiment of this aspect of the invention the alga is a red seaweed of the order Gigartinales, and in a specially preferred embodiment the red seaweed is chosen from the group consisting of *Gracilariopsis lemaneiformis*, *Gracilaria verrucosa* and *Phyllophora truncata*.

In a further preferred embodiment of this aspect of the invention the enzyme is in purified form. In another preferred embodiment the enzyme is in immobilized form. The enzyme can be immobilized on any suitable support materials, such as glass beads, fibers and various polymers.

In a further detailed embodiment the enzyme has an amino acid sequence which comprises at least one of the following fragments:

Fragment 1 (SEQ ID NO: 1), (totally 21 amino acid residues):

| 1 | | | | 5 | | | | | 10 |
|---|---|---|---|---|---|---|---|---|---|
| Tyr(Val) | Met | Val | Pro(Thr) | Asn | Met | Tyr | Tyr | Glu | Asn | His |

| | | 15 | | | | | 20 | |
|---|---|---|---|---|---|---|---|---|
| Gly | Tyr | Glu | Pro | Met Val | Thr | Gln | Tyr | Asn |

Fragment 2 (SEQ ID NO: 2), (totally 30 amino acid residues):

| 1 | | | | 5 | | | | | 10 | |
|---|---|---|---|---|---|---|---|---|---|---|
| Gly | Leu | Val | Pro | Gln | Thr | Asp | Ile | Thr | Pro | Phe | Leu |

| | | 15 | | | | | 20 | | |
|---|---|---|---|---|---|---|---|---|---|
| Arg | Asp | Asn | Asp | Glu | Gly | Gln | Asn | Tyr | Glu | Val | Asn |

| 25 | | | | 30 |
|---|---|---|---|---|
| Gln | Thr | Leu | Arg | Glu | Arg |

-continued

Fragment 3 (SEQ ID NO: 3), (totally 25 amino acid residues):

```
1                    5                   10
Gly(Val) Ala Ala Glu Gln Asn Gly Gly Thr Glu Thr 15                  20
Ile Thr Phe Thr Asp Asn Pro Tyr Arg Tyr Val Phe

25
Gly Gly
```

Fragment 4 (SEQ ID NO: 4), (totally 25 amino acid residues):

```
1                    5
Gly(Ser) Leu Asn Thr(Leu) Tyr Thr Asp Glu Phe(Asp)

10                  15                  20
Pro Leu Val Phe Glu Val Phe Pro Leu Gly Asn Asn
```

In a further detailed embodiment of this aspect of the invention the enzyme has an isoelectric point of around 3.9 and an approximate molecular weight of 111,000 by SDS-gel electrophoresis and 98,000 by gel filtration chromatography and the following approximate amino acid composition determined as amino acid residues per molecule by amino acid analysis:

Asx 155, Thr 71, Ser 57, Glx 94, Pro 49, Gly 98, Ala 52, Cys 15, Val 70, Met 21, Ile 41, Leu 61, Tyr 62, Phe 52, His 16, Lys 37, Arg 48, and Trp not determined.

Another aspect of the invention relates to an enzyme having an approximate molecular weight of 54,000 Da.

Another aspect of the invention is directed to a method of cleaving the terminal α-1,4-D-glucosidic bonds from the non-reducing ends of an α-1,4-glucan, whereby said α-1,4-glucan is brought into contact with an enzyme according to the invention.

In an embodiment of this aspect of the invention the α-1,4-glucan comprises branched chains and the enzyme of the invention is used together with a debranching enzyme, such as pullulanase.

In a preferred embodiment of this aspect of the invention the degradation product comprises 1,5-anhydrofructose.

A further aspect of the invention is directed to 1,5-anhydrofructose for use as an oxygen radical scavenger or anti-oxidant and/or as a substitute for other sugars and their derivatives.

Yet another aspect of the invention is directed to a method of producing an enzyme capable of successively cleaving the terminal α-1,4-D-glucosidic bonds from the non-reducing ends of an α-1,4-glucan, whereby it is isolated from an alga by extraction and purification in per se known manner, or by use of other suitable techniques such as genetic engineering or chemical synthesis making use of a nucleotide sequence coding for an algal α-1,4-glucan lyase or an amino acid sequence related to an algal α-1,4-glucan lyase.

Still another aspect of the invention is directed to an antibody which binds to the amino acid sequence of an enzyme according to the invention.

An additional aspect of the invention is directed to a DNA or RNA probe which recognizes a nucleotide sequence coding for an enzyme according to the invention.

The two last mentioned aspects of the invention are useful in the finding of enzymatically similar derivatives and analogs of the isolated α-1,4-glucan lyase of the invention.

The amino acid sequences of the fragments 1–4 can be used to synthesize DNA or RNA probes. Antibodies which bind to the amino acid sequence of the isolated α-1,4-glucan lyase of the invention has already been prepared.

Starting from the amino acid sequence of the α-1,4-glucan lyase of the invention which has been isolated from an alga, it will be possible to create and/or find enzymatically similar derivatives and analogs. However, since there has been disclosed related enzymatic activity in some fungi, a disclaimer from the scope of protection has been used by establishing that the enzymatically similar "derivatives and analogs" of the α-1,4-glucan lyase are of non-fungal origin.

By using the purified algal enzyme of the invention it was possible to arrive at the following conclusions:

1). The reaction from starch to AF was catalyzed by only one enzyme, the lyase of the invention, not by more enzymes or an enzyme system as postulated by Baute et al. (1988). Besides the substrate and the enzyme, the enzymic reaction does not need any other cofactors or activators. This enzyme is highly specific for α-1,4-glucosidic bonds and releases AF from the non-reducing ends of an α-glucan. It can not degrade endo-α-1,4-glucosidic linkages, α-1,6 and α-1,3 glucosidic linkages or other types of glycosidic linkages.

2). The products (AF, neo-limit dextrin, glucose) and their yield of the enzymic reaction are depending on the type of substrate and its polymerization number (for detail, see formula 1) and 2) supra).

3). The enzyme was a single polypeptide with a molecular weight of 111,000 as observed in SDS-gel electrophoresis, and 98,000 by gel filtration chromatography on Sephacryl S-200.

4). Amino-acid-composition analysis of the enzyme showed high amounts of Asp/Asn, Gly and Glu/Gln.

5). The isoelectric point (pI) of the enzyme was around 3.9, as revealed by isoelectrofocusing.

6). The enzyme can degrade maltose, maltosaccharides, amylose, starch, amylopectin, glycogen and native floridean starch granules.

7). The enzyme exhibited a wide pH optimum range from pH 2.5 to 7.0 for maltose as substrate and from pH 3.5 to 7.5 for amylopectin as substrate.

8). The optimal temperature for activity of the algal enzyme was around 50° C. when maltose or amylopectin was used as a substrate under the assay conditions. The Arrhenius activation energies were 45.8 and 44.0 kJ mol$^{-1}$ for maltose and amylopectin as substrate, respectively.

9). Only one form of this enzyme was found in cell-free extracts of the two red seaweeds. That is, it does not have isozymes.

10). The algal enzyme was strongly inhibited by a glucose analog deoxynojirimycin and sulfhydryl group (—SH) blocking agents, such as $HgCl_2$ and p-chloromercuribenzoic acid (PCMB). The enzyme was also inhibited by maltitol and by amylopectin when maltose was used as a substrate.

11). Antibodies have been raised against the enzyme purified from *Gracilariopsis lemaneiformis* collected in China. These antibodies cross-reacted with the lyases purified from *Gracilariopsis lemaneiformis* collected in Venezuela and *Gracilaria verrucosa* collected in Venezuela.

12). Partial amino acid sequences of α-1,4-glucan lyase with a total length of 101 amino acid residues were obtained. Computer searching through the protein and peptide sequence data banks indicated that these sequences have not been reported before.

13). As the enzyme is new, no routine assay method is available for quantifying the enzyme activity. Two assay methods have now been established, one measuring the release of 1,5-anhydrofructose from maltose or amylopectin by the enzyme, the other measuring the release of glucose when maltose is used as a substrate.

14). 1,5-anhydrofructose (AF) was found to be a sugar of high reducing power, as it can reduce 3,5-dinitrosalicylic acid reagent at room temperature.

15). An efficient purification procedure has been developed for the purification of the enzyme. The key to the success of purification is that it was found that starch can specifically absorb the enzyme. Starch was therefore used as an affinity material and just by one affinity chromatography step, the enzyme was purified to more than 90% purity. The purification factor was 114 and the recovery was over 100%. The enzyme was further purified to homogeneity by chromatography on Q-Sepharose and Sephacryl S-200 columns.

16). The algal enzyme does not show product inhibition, that is, AF, neo-limit dextrin and glucose, which will accumulate during the enzyme reaction, have negligible effect on enzyme reaction rate, and the enzyme reaction can proceed until the substrate is completely degraded. In an enzyme concentration of 6 µg protein per ml, at 30° C., the time needed for a complete degradation of 1% maltose solution was 1 h, for 2% maltose solution 3 h, for 5% maltose solution, 10–24 h, for 2% maltoheptaose, 10–24 h. This is in sharp contrast to many polysaccharides' depolymerization enzymes, whose reaction stops with the accumulation of products or with the decrease in substrate size.

Simple Steps for the Production of Highly Purified AF

A: Using soluble starch as starting material. An aqueous soluble-starch solution (2%) is incubated at 30° C. for 24 hours in the presence of 5.2 µg α-1,4-glucan lyase per ml reaction mixture. The yield of AF is 55%. Highly purified AF can be simply obtained by passing the reaction mixture through a Sephadex G-25 column. In this column, AF (molecular weight=162.14) can be well separated from neo-limit dextrin whose molecular weight is several thousands or more.

In the above reaction mixture, if the debranching enzyme pullulanase in a concentration of 1.2 Units per ml reaction mixture is added, the yield of AF increases to 73%.

B: Using amylopectin as starting material. Amylopectin (2%) is incubated at 30° C. for 24 hours in the presence of 5.2 µg α-1,4-glucan lyase per ml aqueous reaction mixture. The yield of AF is 53%. Highly purified AF can be obtained as described above. In the presence of pullulanase of 1.2 Units per ml reaction mixture, the yield of AF increases to 80%.

Note, pullulanase is a commercially available enzyme. It is used together with β-amylase in industry for large scale production of maltose from starch. In our experiments, we found that our enzyme can function cooperatively with pullulanase for the increasing of the yield of 1,5-anhydrofructose by 18 to 27%, depending on whether soluble starch or amylopectin is used as a substrate.

[In contrast, the AF preparation obtained by Baute et al. (1988, page 3403) contained a lot of impurities. They had to add yeast cells to consume the glucose in their AF preparation and then separate the yeast Cells. The AF preparation was then passed through an ion exchange column. As they did not have a method to quantify AF, they had to use TLC or HPLC for monitoring the AF peak in the chromatography. By this step, their purity was only 90%. Highly purified AF was obtained by separation on TLC plates. AF spot was then extracted from the Silica gel. As they reported, the final AF yield was 40–50%. It is obvious that their methods for production of AF are tedius and complex, and not suitable for pilot scale or large scale production of highly purified AF.]

17). The enzyme is very stable (at 4° C. for 1 year without apparent loss of activity) and can be lyophilized as dried powder.

All these above-mentioned properties make this algal enzyme very suitable for industrial production of AF and neo-limit dextrin, such as its wide pH optimum, stability and lack of product inhibition. The enzyme can be purified from algae, which are famed all over the world. Alternatively, the enzyme can be produced by bacteria through recombinant DNA techniques. As an approach to this, around 10% of the amino acid sequences of the enzyme has been analyzed so far. These sequences will facilitate the work towards obtaining the whole nucleotide sequence of the enzyme.

Utility of the Enzyme of the Invention

A. The enzyme can be used as an analytical reagent:

1). To determine the contents of maltosaccharides (including maltose) and amylose in samples. The principle is that the product of the enzyme reaction, 1,5-anhydrofructose (AF), can react with dinitrosalicylic acid reagent and the reaction finishes within several minutes at room temperature. The reaction mixture has an absorbance peak at 546 nm. The absorbance is proportional to the amount of AF present. This method offers rapidity, simplicity and reasonable sensitivity.

2). For the determination of polysaccharide structure. This enzyme is strict for the degradation of α-1,4-glucosidic linkage and degrades the polysaccharides from their non-reducing ends.

B. The enzyme can be used for the production of AF and neo-limit dextrin:

1). For the production of AF. AF is a sugar with high reducing capability and can therefore be used as an oxygen radical scavenger in medicine and as anti-oxidant in the food industry. Examples of industries where anti-oxidants are used are the oil and fat industry, the food industry and the cosmetics and medical industries. AF can be used as a substitute for other sugars and sugar derivatives, such as fructose, sorbitol, xylitol etc.

2). For the production of neo-limit dextrin. Neo-limit dextrin is a specific substrate for α-amylase assay. When amylopectin is used as a substrate, besides AF as the reaction product, another product is a neo-limit dextrin, which has only one glucose unit on the branches, and therefore it is resistant to the hydrolysis of β-amylase and α-glucosidase. α-Amylase activity is routinely assayed in the brewery industry, agronomy and in research. The substrate available on the market now is a β-limit dextrin obtained by β-amylase-hydrolyzation of amylopectin. However, there are 1–3 glucose units at the branching points (α-1,6-linkages) and therefore it is also prone to hydrolysis by α-glucosidase.

DETAILED CHARACTERIZATION OF THE ENZYME

Enzyme Purification

1). Starch was a powerful affinity medium for the purification of the red algal α-1,4-glucan lyase, as the enzyme activity peak Just overlapped the absorbance peak of the enzyme protein at 280 nm. As revealed by SDS-PAGE, the enzyme preparation after this starch column, showed one α-1,4-glucan lyase band, and one faint band of a contaminating protein. This contaminating protein had a molecular weight of 97,000, and was visible only when the sample was overloaded. It was eliminated by subsequent gel filtration chromatography on Sephacryl S-200. α-1,4-Glucan lyase was purified to homogeneity by these procedures as revealed by silver staining. The specific activity of the purified α-1,4-glucan lyase was 93.3 U mg$^{-1}$ protein. The recovery rate after the starch column was usually greater than 100% and the purification factor was of 114 (Table I):

TABLE I

Purification of α-1,4-glucan lyase from *Gracilariopsis lemaneiformis*

| Fraction | Total Activity (U) | Total Protein (mg) | Specific Activity (U mg$^{-1}$) | Fold | Yield (%) |
|---|---|---|---|---|---|
| 1. Cell-free extract | 21.2 | 65.8 | 0.322 | 1 | 100 |
| 2. Starch column | 24.7 | 0.673 | 36.7 | 114 | 116 |
| 3. Sephacryl S-200 | 16.1 | 0.172 | 93.3 | 290 | 76 |

At pH 6.6, α-1,4-glucan lyase was able to specifically adsorb onto the starch column so tight that 1M NaCl in buffer A (50 mM citrate-NaOH (pH 6.6)) failed to deadsorb it. α-1,4-Glucan lyase could, however, be eluted by amylopectin, glycogen, and maltoheptaose in a concentration of 8 mg ml$^{-1}$. Pullulan, maltose, and maltotetraose were less effective for the elution of the enzyme from starch column (Table II), while glucose was totally ineffective. In these experiments, as much as 5 times of the column volume was collected. At high pH, for example, 50 mM bicine-NaOH (pH 8.2), the binding of the enzyme onto the starch column was loose and it was eluted by subsequent washing with the same buffer. Neither ConA-Sepharose nor cycloheptaamylose-Sepharose 6B was effective for the purification of the enzyme because of low recovery.

TABLE II

The efficiency of various glucans (8 mg ml$^{-1}$) on the elution of α-1,4-glucan lyase from the starch column. The column volume was 1 ml and 5 ml eluate was pooled. The recovery of α-1,4-glucan lyase eluted by amylopectin was used as 100%.

| Glucan | Elution Efficiency (%) |
|---|---|
| Glucose | 0 |
| Maltose | 56.4 |
| Maltotetraose | 65.7 |
| Maltoheptaose | 94.3 |
| Pullulan | 32.3 |
| Glycogen | 87.1 |
| Amylopectin | 100 |

2). The molecular weight of the red algal lyase of the invention

The molecular weight of the algal α-1,4-glucan lyase was 111,000 as estimated by SDS-PAGE. Its native molecular weight was 98,000 by gel filtration. α-1,4-Glucan lyase may form dimer or oligomer, since enzymic forms of higher molecular weights have been observed during purification. But the monomer of the enzyme was always the dominating form. In cell-free extract, only the monomer form was observed.

For active staining using I$_2$/KI solution, α-1,4-glucan lyase band appeared as a clear area against the dark blue background of the gel. After a couple of days in 5% HAc and 10% (v/v) glycerol, the background of the gel faded and turned clear while the marker proteins and enzyme bands became stained and appeared as yellow to blue bands. The sensitivity is near that of PhastGel Blue R.

3). Isoelectric point (pI) and amino acid composition of the red algal lyase of the invention The algal α-1,4-glucan lyase had an acidic pI of around 3.9, close to the pI of the marker enzyme amyloglucosidase which is 3.5. Amino acid composition analysis of the enzyme showed high contents of Asp/Asn, Gly, and Glu/Gln, and a low content of cysteine (Table III).

TABLE III

Amino acid composition of the algal α-1,4-glucan lyase of the invention. A molecular weight of 111,000 observed in SDS-PAGE gels was used for the normalization of data.

| Amino acid | Number of residues/molecule |
|---|---|
| Asx* (Aspartic acid) | 155 |
| Thr (Threonine) | 71 |
| Ser (Serine) | 57 |
| Glx** (Glutamic acid) | 94 |
| Pro (Proline) | 49 |
| Gly (Glycine) | 98 |
| Ala (Alanine) | 52 |
| Cys (Cysteine) | 15 |
| Val (Valine) | 70 |
| Met (Methionine) | 21 |
| Ile (Isoleucine) | 41 |
| Leu (Leucine) | 61 |
| Tyr (Tyrosine) | 62 |
| Phe (Phenylalanine) | 52 |
| His (Histidine) | 16 |
| Lys (Lysine) | 37 |
| Arg (Arginine) | 48 |
| Trp (Tryptophan) | Not determined |

*Asx is the sum of aspartic acid and asparagine.
**Glx is the sum of glutamic acid and glutamine.

4). pH optimum

The α-1,4-glucan lyase had a wide pH optimum range, from pH 2.5 to 7.0, when maltose was used as a substrate. The enzymic activity decreased dramatically in pH values lower than 2.5 and higher than 7.0 and to minimum at pH 1.9 and 8.9. In the optimal pH range, α-1,4-glucan lyase showed similar activity in glycine-HCl (1.9–3.4), HAc-NaAc (3.7–5.9), Mops-NaOH (6.1–8.0), and bicine-NaOH (7.2–8.9), and slightly lower activity in citrate-NaOH (5.1–8.6). When amylopectin was used as a substrate, the pH optimal range was 3.5 to 7.5, showing an alkaline shift when compared to the case when maltose was used as a substrate. Also, in the case of amylopectin, the enzymic activity decreased gradually with decreasing pH in glycine-HCl, which is in sharp contrast to the case when maltose was used.

5). The optimal temperature and stability

The optimal temperature for α-1,4-glucan lyase was around 50° C. when maltose or amylopectin was used as a substrate. The enzymic activity was the lowest at 3.5° C. In the case of amylopectin, enzymic activity decreased by 50% at 33° C. and 65° C. At 70° C., the enzyme still showed some residual activity. When the enzyme was heated to 70° C. in the absence of substrate, the activity was lost completely after 5 min. These facts point to a certain degree of protection effect of the substrate against heat denaturation of the enzyme. The calculated Arrhenius activation energies (Ea) were 45.8 and 44.0 kJ mol$^{-1}$ for maltose and amylopectin, respectively. The temperature coefficients ($Q_{10}$) from 30° to 40° C. were 1.84 for maltose and 1.79 for amylopectin.

6). The enzyme purified from other red algae

Activity of α-1,4-glucan lyase was detected in *Gracilariopsis lemaneiformis* (GLv) and *G. verrucosa* (GVv) collected from Araya Peninsula, Venezuela. α-1,4-Glucan lyases were purified from the two Venezuelan species using the same procedure developed from *Gracilariopsis lemaneiformis* (GLc) collected from Qingdao, China. The lyases purified from GLv and GVv shared the following properties with the lyases from GLc:

1. The lyases from GLv and GVv displays the same molecular mass as measured under both denatured conditions on SDS-PAGE and non-denaturing conditions on native-PAGE using gels with a gradient of 8–25%.
2. Antibodies raised against the lyase from GLc cross-reacted with the lyases purified from GLv and GVv, indicating the lyases from different species shared common antigen determinants.
3. The lyases purified from GLv and GVv also degraded α-glucans and released AF as the lyase from GLc.
4. As in the case of the lyase from GLc, the lyases from GLv and GVv were stable at 0°–4° C.
5. The lyases from GLv and GVv were also able to adsorb onto a starch column and were later eluted with dextrins. The lyases from GLv and GVv were purified with high efficiency and high recovery rate using the purification method developed for GLc.

The results listed above indicate that the lyases from the three red seaweeds are coded by either the same gene or different genes of high homology among them. If they are coded by different genes, the differences among these genes may be trivial and minor, so that primary amino acid sequences among the lyases are also highly similar. Conservative replacement of certain amino acid residues, minor deletions and insertions may occur in the primary amino acid sequences of the lyases, but they do not affect the conformation and function of the enzyme appreciably.

7). Substrate specificity and reaction mode

When amylopectin was used as a substrate, the activity reached maximum 8 mg ml$^{-1}$ and then decreased slightly at 20 mg ml$^{-1}$. The same results were obtained with soluble starch and maltoheptaose. When maltotriose and maltose were used as substrates, the activity reached maximum at 2 mg ml$^{-1}$ and 6 mg ml$^{-1}$, respectively. Substrate inhibition became evident at higher concentrations, especially in the case of maltotriose. Like maltotriose and maltose, maltotetraose, maltopentaose and maltohexaose all showed substrate inhibition. Generally, the inhibition degree decreased with the increase in DP number (Degree of Polymerization). When the activity measured at 10 mg ml$^{-1}$ was compared at 2 mg ml$^{-1}$ and 4 mg ml$^{-1}$, substrate inhibition could be clearly seen among the maltosaccharides of DP 3–5. In maltohexaose, the substrate inhibition was very low and was none in maltoheptaose. Among the maltosaccharides, maltotetraose and maltopentaose were the poorest substrates.

α-1,4-Glucan lyase was examined with respect to its ability to degrade a variety of substrates (Table IV). α-1,4-Glucan lyase degraded maltoheptaose at similar rate to those obtained with amylopectin, amylose, and soluble starch; but it was less active with β-limited dextrin, glycogen and floridean starch. With PNPG1 (p-nitrophenyl-α-D-glucoside), the artificial substrate of α-glucosidase, reaction rate was the lowest. No 1,5-anhydrofructose and glucose were released as checked by TLC on Silica gel 60 after 24 h of incubation with isomaltose (α-D-Glc-[1-6]-α-D-Glc), trehalose (α-D-Glc-[1-1]-α-D-Glc), cellobiose (β-D-Glc-[1-4]-β-D-Glc), sucrose (α-D-Glc-[1-2]-β-D-Fru), lactose (β-D-Gal-[1-4]-β-D-Glc), melibiose (α-D-Gal-[1-6]-α-D-glucose), methyl α-D-glucoside and cyclohexaamylose (Table V).

Cyclohexaamylose and methyl α-glucoside showed also no inhibitory effect on the enzyme activity at a concentration of 4 mM and 12 mM, respectively, when maltose or soluble starch was used as a substrate. That the enzyme activity increased with the size of the substrate in the case of methyl-α-D-glucoside, PNPG1, maltose, PNPG2 (p-nitrophenyl-α-D-maltoside) and PNPG7 (p-nitrophenyl-α-D-maltoheptaoside) from zero to maximum implies that the enzyme needs a certain size of the substrate for binding before catalysis can be exerted. The algal α-1,4-glucan lyase also showed no detectable activity with pullulan and sulfated galactan. At such long term incubation at 30° C., however, α-1,4-glucan lyase was able to degrade nigerose (α-D-Glc-[1-3]-α-D-Glc), and panose (α-D-Glc-[1-6]-α-D-Glc-[1-4]-α-D-Glc). Only very low degrading rate was observed with BPNPG7 (blocked p-nitrophenyl-α-D-maltoheptaoside) (Table V). However, the reaction rates presented in Table V must be regarded as trivial in relation to those in Table IV.

TABLE IV

Substrate Specificity of α-1,4-Glucan lyase.
The concentration of various substrates in the reaction mixture was 10 mg ml$^{-1}$ except PNPG1, PNPG2, PNPG7, which was 2 mM. The incubation time was 15 min. The degrading rate of maltoheptaose was 84 μmol min$^{-1}$ mg$^{-1}$ protein.

| Substrate | Activity (% of Maltoheptaose) |
| --- | --- |
| Maltose | 66.7 |
| Maltotriose | 39.1 |
| Maltotetraose | 27.8 |
| Maltopentaose | 36.6 |
| Maltohexaose | 74.6 |
| Maltoheptaose | 100.0 |
| β-Limit dextrin | 22.7 |
| Glycogen | 77.6 |
| Amylopectin | 94.1 |
| Amylose | 100.4 |
| Soluble starch | 100.2 |
| Floridean starch | 61.9 |
| PNPG1 | 0.113 |
| PNPG2 | 22.5 |
| PNPG7 | 100.0 |

TABLE V

Continuation of Table IV.
For BPNPG7, the reaction mixture contained 4.91 μg enzyme and 1.64 μg for the others. The incubation time was 24 h.

| | Substrate Conc. | Product released (nmol) |
| --- | --- | --- |
| Native floridean starch granules | 4 mg ml$^{-1}$ | 323.2 |
| | 10 mg ml$^{-1}$ | 1323.2 |
| Nigerose | 4 mg ml$^{-1}$ | 13452.8 |
| Panose | 4 mg ml$^{-1}$ | 13465.6 |
| Maltitol | 4 mg ml$^{-1}$ | 122.4 |
| BPNPG7 | 2 mM | 6.16 |
| Isomaltose | 4 mg ml$^{-1}$ | 0 |
| Trehalose | 10 mg ml$^{-1}$ | 0 |
| Cellobiose | 4 mg ml$^{-1}$ | 0 |
| Sucrose | 10 mg ml$^{-1}$ | 0 |
| Lactose | 10 mg ml$^{-1}$ | 0 |
| Melibiose | 10 mg ml$^{-1}$ | 0 |
| Methyl α-D-glucoside | 10 mM | 0 |
| Cyclohexaamylose | 20 mM | 0 |
| Pullulan | 4 mg ml$^{-1}$ | 0 |
| Sulfated galactan of *Gracilaria sordida* | 10 mg ml$^{-1}$ | 0 |
| PNPMan | 2 mM | 0 |
| PNPGal | 2 mM | 0 |
| Glucose 1-Phosphate | 10 mM | 0 |
| ADP-Glucose | 5 mM | 0 |
| UDP-Glucose | 7.6 mM | 0 |

The inability of the algal α-1,4-glucan lyase to degrade cyclohexaamylose and pullulan (which is a linear polymer containing maltotriose repeating units linked by α-1,6-linkages) suggests that it has little or no endo-cleavage activity.

The algal lyase apparently starts its lyric action of a α-1,4-glucan chain from the non-reducing end, as it showed little or no activity towards panose, BPNPG7 and pullulan. (BPNPG7 is a non-reducing end blocked nitrophenyl maltoheptaose and a substrate specially designed for the determination of endoamylolytic activity). The very low activity with BPNPG7 is not due to the presence of nitrophenyl group bonded at the reducing ends, as in the case of PNPG7, an activity as high as maltoheptaose was observed.

From the Tables IV and V, it can also be concluded that the algal lyase is highly specific for a α-1,4-glucosidic bond, and shows no activity towards other analogs of α-glucosides, such as PNPGman (p-introphenyl-α-D-mannoside) and PNPGal (p-nitrophenyl-α-D-galactoside), which are modified by inversion of hydroxyls of C-2 (mannose) or C-4 (galactose), respectively.

The algal α-1,4-glucan lyase can readily degrade heat-denatured floridean starch isolated from the same plant, from which the enzyme was purified (Table IV). The rate was, however, lower than soluble starch and amylopectin. This may be due to the high viscosity of the floridean starch solution compared to soluble starch. The reaction mixture containing boiled floridean starch was more whitish than those of boiled soluble starch or other substrates.

The algal enzyme does not show product inhibition, that is, AF, neo-limit dextrin and glucose, which will accumulate during the enzyme reaction, have negligible effect on enzyme reaction rate, and the enzyme reaction can proceed until the substrate is completely degraded. In an enzyme concentration of 6 μg protein per ml, at 30° C., the time needed for a complete degradation of 1% maltose solution was 1 h, for 2% maltose solution, 3 h, for 5% maltose solution, 10–24 h, for 2% maltoheptaose, 10–24 h. This is in sharp contrast to many polysaccharides' depolymerization enzymes, whose reaction stops with the accumulation of products or with the decrease in substrate size.

The algal lyase removes glucose unit as 1,5-anhydrofructose successively from the non-reducing ends of α-glucan molecules until last glucose unit is left (in the case of a linear glucan) or until it comes across a branch point where glucose unit is linked by bonds other than α-1,4. It can not convert monosaccharides, such as fructose, glucose, galactose and mannose to 1,5-anhydrofructose. When maltoheptaose was used as a substrate, the final products are 1,5-anhydrofructose and glucose and their ratio is 6:1. The intermediate products are a mixture of maltosaccharides with a DP number between 2–6 during the process of the reaction. With the increase of reaction time, the DP number of the maltosaccharides decreased and finally all the maltosaccharides disappeared. When maltose was used as a substrate, the ratio of 1,5-anhydrofructose to glucose was 1:1. With the increase of DP number, the yield of glucose decreased, while the yield of 1,5-anhydrofructose increased. When a linear chain of a α-1,4-glucan is long enough, the yield of 1,5-anhydrofructose can be nearly 100%.

When branched glucans are used as substrates, apart from 1,5-anhydrofructose, another enzyme reaction product is limit dextrin, which is tentatively called neo-limit-dextrin. The yield of 1,5-anhydrofructose and neo-limit-dextrin depends on the percentage of the length of linear chain starting from the non-reducing ends of a macro-glucan molecule. Neo-limit-dextrin is characterized by having only one glucose unit on the α-1,6 linkage point and therefore it is resistant to hydrolysis of α-glucosidase. So it is more ideal as a substrate for the specific assay of α-amylase than β-limit dextrin, which is produced by β-amylase hydrolyzation on amylopectin and has been marketed. β-Limit dextrin may have 2–3 glucose units on the side chain linked by α-1,6-bonds to the backbone chain and therefore is prone to the hydrolysis by α-1,4-glucan lyase (Table IV) and α-glucosidase.

8). Specificity of the rabbit-anti α-1,4-glucan lyase serum.

Reaction of α-1,4-glucan lyase against its immune serum was checked by double diffusion in agar plates, by the neutralization of enzymic activity, and by Western blotting. α-1,4-Glucan lyase (3.9 μg protein) gave a single white precipitin band when tested against a 1:64 dilution of the immune serum. Precipitin bands were also observed when α-1,4-glucan lyase purified from *Gracilariopsis lemaneiformis* collected from Venezuela or *Gracilaria verrucosa* were tested.

When α-1,4-glucan lyase was measured in the presence of the immune serum, 50% inhibition of the enzymic activity occurred at a level of 2 μl and 3 μl immune serum, respectively, when amylopectin or maltose was used as a substrate, and 94% inhibition occurred in the presence of 8 μl immune serum in the case of both maltose and amylopectin. Results from Western blotting further confirmed the specificity of the antibodies, as only one band in the cell-free extract which corresponded to the lyase was recognized by the antibodies.

9). Inhibition studies

A. Sugars and sugar analogs

1) Deoxynojirimycin, an analog of glucose, completely inhibited the enzyme activity at a concentration of 2 mM whether maltose or amylopectin was used as substrate. Further experiments showed that even 0.165 mM of the inhibitor was able to inhibit the activity completely when maltose was used as a substrate.

2) Maltitol, an analog of maltose, at a concentration of 0.1M inhibited the enzymic activity by around 47% and 27% when maltose and amylopectin were used as substrate, respectively. It was further shown that the inhibition by maltitol to maltose as substrate was typically competitive. That is, the inhibitor maltitol competes for the same binding site in the enzyme as the substrate maltose.

3) Glucose, inhibited the enzymic activity by around 22% at a concentration of 0.1M when maltose was used as a substrate, while at such concentration, it showed no inhibition when amylopectin was used as a substrate.

4) Other sugars, at a concentration of 0.1M, showed no inhibition whether maltose or amylopectin was used as a substrate. These sugars include: glycerol, xylose, arabinose, fructose, mannose, galactose, sucrose, lactose, melibiose, trehalose, inositol, and sorbitol.

B. Polysaccharides

The degradation of maltose by the enzyme lyase was inhibited by around 67% and 47% in the presence of 3 mg/ml amylopectin and glycogen, respectively. Further experiments showed that the inhibition to the degradation of maltose by amylopectin was of mixed competive/non-competive type. Pullulan did not inhibit the activity.

C. Sulfhydryl group (—SH) blocking agents p-Chloromercuribenzoic acid (PCMB) at a concentration of 2 mM inhibited the enzyme activity by around 90% whether maltose or amylopectin was used as a substrate. Similar inhibition was observed in the presence of $HgCl_2$ at a concentration of 10 mM. These experiments indicated that sulfhydryl group(s) are vital for the enzymic activity.

D. Salt ions

KCl, CaCl$_2$, MnCl$_2$, MgCl$_2$, all showed no inhibition to the enzyme at a concentration of 50mM, whether maltose or amylopectin was used as a substrate.

10). The reducing power of 1,5-anhydrofructose (AF)

Table VI shows the time course reduction of 3,5-dinitrosalicylic acid (DNS) reagent by AF as monitored by the absorbance at 546 nm. It can be seen that the reaction was completed in less than 10 minutes. This is in sharp contrast to other reducing sugars, such as glucose and maltose, whose reaction with DNS reagent is completed at 100° C. for 5 min ((Steup, M. (1990) Methods in Plant Biochemistry (Dey, P. M. and Harborne, J. B., eds.), Vol.3, pp. 103–127, Academic Press, London).

TABLE VI

Time-course reaction of AF with DNS reagent at room temperature. The absorbance at 546 nm as a measure of reaction rate was recorded soon after the addition of 300 µl DNS reagent to 300 µl sample solution containing varying amount of AF.

| Reaction Time | AF content (µmol) | | | |
| --- | --- | --- | --- | --- |
| (min) | 0.55 | 1.26 | 2.36 | 2.84 |
| 0 | 0 | 0 | 0 | 0 |
| 1 | 0.037 | 0.218 | 0.476 | 0.559 |
| 2 | 0.180 | 0.468 | 0.930 | 1.222 |
| 3 | 0.274 | 0.660 | 1.271 | 1.628 |
| 4 | 0.341 | 0.796 | 1.510 | 1.898 |
| 5 | 0.386 | 0.888 | 1.671 | 2.070 |
| 6 | 0.414 | 0.948 | 1.775 | 2.176 |
| 7 | 0.431 | 0.985 | 1.840 | 2.239 |
| 8 | 0.440 | 1.007 | 1.880 | 2.278 |
| 9 | 0.444 | 1.024 | 1.905 | 2.300 |
| 10 | 0.446 | 1.029 | 1.920 | 2.311 |

11). Methods established for the assay of the enzyme

As this α-1,4-glucan lyase is a new enzyme, methods for routine activity analysis are lacking. Two methods were therefore developed for the determination of α-1,4-glucan lyase activity.

Method 1 (The DNS Method)

α-1,4-Glucan lyase breaks downstarch-like molecules to produce 1,5-anhydrofructose (AF), which is heat-stable and possesses reducing power. The reaction of AF with 3,5-dinitrosalicylic acid reagent occurred at room temperature and was completed within 10 min (Table VI). A linear relationship exists for AF between the absorbance of 0.1–2.3 at 546 nm and AF content, ranging from 0.3–2.7 µmol or 50–440 µg i 300 µl sample (Table VII). The presence of substrate levels of maltose, amylopectin and the other enzymic reaction products, neo-limit dextrin and glucose, did not interfere the reaction under the conditions described. This method is applicable to both the smallest substrate as maltose and the largest substrate as amylopectin.

TABLE VII

The correlation between AF content and absorbance. Absorbance was measured 10 min after the addition of 300 µl DNS reagent to 300 µl sample solution containing varying amount of AF as indicated.

| AF content (µmol) | Absorbance (546 nm) |
| --- | --- |
| 0 | 0 |
| 0.264 | 0.113 |

TABLE VII-continued

The correlation between AF content and absorbance. Absorbance was measured 10 min after the addition of 300 µl DNS reagent to 300 µl sample solution containing varying amount of AF as indicated.

| AF content (µmol) | Absorbance (546 nm) |
| --- | --- |
| 0.340 | 0.154 |
| 0.360 | 0.166 |
| 0.526 | 0.305 |
| 0.540 | 0.237 |
| 0.636 | 0.355 |
| 0.655 | 0.514 |
| 0.702 | 0.584 |
| 0.929 | 0.682 |
| 1.089 | 0.710 |
| 1.148 | 0.880 |
| 1.181 | 0.880 |
| 1.241 | 1.099 |
| 1.514 | 1.415 |
| 1.529 | 1.260 |
| 1.588 | 1.516 |
| 1.627 | 1.302 |
| 1.712 | 1.409 |
| 2.031 | 1.830 |
| 2.052 | 1.703 |
| 2.183 | 1.806 |
| 2.241 | 1.787 |
| 2.362 | 1.875 |
| 2.683 | 2.266 |
| 3.221 | 2.590 |

Method 2 (The Enzymatic Method)

The activity of α-1,4-glucan lyase can be analyzed by quantifying glucose released. This is based on the observation that AF and glucose are produced on an equal mole basis when maltose is used as a substrate. The glucose released (in the range of 10–100 nmol in 300 µl reaction system) was determined enzymatically either by monitoring the reduction of NADP at 340 nm in the presence of hexokinase and glucose 6-phosphate dehydrogenase or by the glucose oxidase-peroxidase system. The presence of AF, maltose did not interfere the quantification of glucose. These enzymatic methods were around 6–10 times more sensitive than the direct measurement of AF, but they are not applicable to large glucan molecules as substrates.

12). AF can be used as a substitute for other sugars and sugar derivatives. AF can not be metabolized through hexokinase and glucose-6-phosphate dehydrogenase pathway and neither by glucose peroxidase. AF can therefore be regarded as a non-metabolizable sugar in living organisms that lack this new starch/glycogen degradation pathway catalyzed by the α-1,4-glucan lyase. It may be added in foodstuffs (including sweets/candies) to reduce their calories.

13). Partial amino acid sequences of the enzyme

After hydrolyzation of the enzyme by proteinase, the hydrolyric fragments of the enzyme was separated on HPLC as described in the Materials and Methods section and used to obtain internal N-terminal sequences. Four sequences with totally 101 amino acid residues were obtained. Each of the obtained sequences were compared with totally 65,342 known protein and peptide sequences by searching the data banks PIR 32 and Swiss-Prot 22. The result of the searching indicated that these sequences of the new enzyme have not been reported before. The following are the results of these sequences analysis.

Amino acids (expressed in three letter symbols):

Fragment 1 (SEQ ID NO: 1), (totally 21 amino acid residues):

```
1                          5                     10
Tyr(Val) Met Val Pro(Thr) Asn Met Tyr Tyr Glu Asn His
              15                    20
Gly Tyr Glu Pro Met Val Thr Gln Tyr Asn
```

Fragment 2 (SEQ ID NO: 2), (totally 30 amino acid residues):

```
1                      5                       10
Gly Leu Val Pro Gln Thr Asp Ile Thr Pro Phe Leu
               15                    20
Arg Asp Asn Asp Glu Gly Gln Asn Tyr Glu Val Asn
25                  30
Gln Thr Leu Arg Glu Arg
```

Fragment 3 (SEQ ID NO: 3), (totally 25 amino acid residues):

```
1                          5                      10
Gly(Val) Ala Ala Glu Gln Asn Gly Gly Thr Glu Thr
               15                    20
Ile Thr Phe Thr Asp Asn Pro Tyr Arg Tyr Val Phe
25
Gly Gly
```

Fragment 4 (SEQ ID NO: 4), (totally 25 amino acid residues):

```
1                          5
Gly(Ser) Leu Asn Thr(Leu) Tyr Thr Asp Glu Phe(Asp)
10                   15                    20
Pro Leu Val Phe Glu Val Phe Pro Leu Gly Asn Asn
```

Materials and Methods Used for the Purification and Characterization of the New Enzyme

Materials

*Gracilariopsis lemaneiformis* (Bory) Dawson, Acleto et Foldvik (*Gracilaria lemaneiformis* (Bory) Weber-van Bosse) and *Gracilaria verrucosa* (Huds.) Papenf. were collected from Araya Peninsula, Sucre, Venezuela, in September 1990. *Gracilariopsis lemaneiformis* was also collected from Zhan Shan Bay, Qingdao, China, in March, 1990. Since then, these plants have been cultivated unialgallyin the laboratory. Glycogen (rabbit liver), amylopectin (potato), maltosaccharides, were from Sigma Chemical Co., soluble starch from E. Merck. All other chemicals were from Pharmacia LKB Biotec. AB.

Methods

Isolation and purification of α-1,4-glucan lyase

*Gracilariopsis lemaneiformis* (originally collected from China), 30 g, was sampled directly from the culture cylinder and was rinsed briefly with deionized water and blotted dry with paper tissue. The following operations were carried out at 0°–4° C. The thalli were cut to pieces with scissors and pulverized under liquid nitrogen. To 1 g alga powder was added 3 volumes of buffer A (50 mM citrate-NaOH, pH 6.6), filtered through two-layer cloth and centrifuged at 36,600×g for 10 min. The supernatant (cell-free extract) was loaded onto a starch column (4.1×1.5 cm) pre-equilibrated with buffer A. After loading, the column was extensively washed with 4 volumes of buffer A, volumes of buffer A containing 1M NaCl, 1 volume of buffer A, 1 volume of buffer B (50 mM imidazole-HCl, pH 6.6) in a flow speed of 24 ml h$^{-1}$. α-1,4-Glucan lyase was eluted with buffer B containing 10 mg ml$^{-1}$ amylopectin in a fraction size of 3.5 ml. To separate α-1,4-glucan lyase from the amylopectin, the active fractions of the eluate were pooled and applied onto a Q-Sepharose column (2.6×5 cm). The column was pre-equilibrated and later washed with buffer B. α-1,4-Glucan lyase was eluted with buffer B containing 0.7M NaCl. Active fractions were pooled and concentrated on a Centriprep CP30 (Amicon, USA) with a molecule weight cutoff of 30,000 and applied to a Sephacryl S-200 column (2.6×80 cm) pre-equilibrated and eluted with buffer A containing 0.2M NaCl. The flow speed was 60 ml h$^{-1}$ with a fraction size of 3.5 ml per tube. Active fractions were collected and concentrated again by using centriprep CP30. A summary of the purification is given in Table I Supra.

The Sephacryl S-200 column (2.6×80 cm) was calibrated with gel filtration protein markers of ribonuclease A (13,700), chymotrypsinogen A (25,000), ovalbumin (43,000), albumin (67,000), aldolase (158,000), catalase (232,000), ferritin (440,000), and thyroglobulin (669,000) as described in Plant. Physiol. and Biochem. 29, 341–347 by Yu, S., and Pedersén M.(1991). The mol wt of α-1,4-glucan lyase was estimated from its partition coefficient, relative to the marker proteins. The affinity medium cycloheptaamylose-Sepharose 6B was prepared by coupling cycloheptaamylose with Epoxy-activated Sepharose 6B according to Vretblad as described by Preiss, J. Okita, T. W. and Greenberg, E. (1980) Plant Physiol. 66: 864–869.

Assay of α-1,4-glucan lyase

The reaction mixture for the assay of α-1,4-glucan lyase was composed of 240 μl 62.5 mM Mops-NaOH containing 6 mg soluble starch (pH 6.2), the enzyme preparation and distilled water to a final volume of 300 μl. The reaction was carried out at 30° C. for 10–30 min. Liberated 1,5-anhydrofructose was determined by monitoring the absorbance at 546 nm after the addition of 3,5-dinitrosalicylic acid reagent. Soluble starch in the reaction mixture may be replaced by other substrates and the final substrate concentration may be varied as indicated in the text. The reaction time and enzyme concentration used in enzyme activity assay have been chosen to ensure the linearity of the reaction rate. One unit of α-1,4-glucan lyase activity is defined as the amount of enzyme which liberates 1μmol of 1,5-anhydrofructose min$^{-1}$ under the conditions described above.

Electrophoresis

Both SDS- and native gradient gel electrophoreses as well as isoelectrofocusing and subsequent staining with PhastGel Blue R and silver were performed by using PhastSystem™ (Pharmacia LKB Biotec. AB, Bromma, Sweden) and pre-cast gels with a gel gradient of 8–25% according to the manufacturer's instructions. The buffer system consisted of 0.112M acetate-0.112M Tris, pH 6.4 in the gel, and 0.2M tricine-0.2M Tris, pH 7.5 containing 0.55% SDS in the buffer strips (electrode buffer) for SDS-gel electrophoresis or 0.88M L-alanine-0.25M Tris, pH .8.8 for native gel electrophoresis. Protein markers used for the estimation of the mol wt of α-1,4-glucan lyase in SDS-PAGE were: myosin (212,000), α$_2$-macroglobulin (170,000), β-galactosidase (116,000), transferrin (76,000), and glutamate dehydrogenase (53,000), and in native gradient PAGE were: thyroglobulin (669,000), ferritin (440,000), catalase (232,000), lactate dehydrogenase (140,000) and albumin (67,000). Pre-cast gels with a pH gradient of 3–9 was used for isoelectro-focusing. The pI of α-1,4-glucan lyase was estimated from the calibration curve of the pI values of marker proteins versus their migration distance from cathode in mm. For activity staining, electrophoresis was performed at 6° C. At the end of electrophoresis, the gel was directly placed in 0.1M citrate-NaOH buffer (pH 6.0) containing 20 mg ml$^{-1}$ soluble starch and incubated at 30°

C. overnight. The gel was then rinsed in distilled water and stained with I$_2$/KI solution (stored at 4° C.) in a concentration of 10 and 14 mM, respectively. The gel was stored in 5% HAc and 10% glycerol at room temperature in the dark. α-1,4-Glucan lyase band was observed as clear area against dark blue background immediately after staining. Protein bands were seen in a couple of days' time as yellow to blue bands in contrast to the faded background.

Western Blotting

Western blotting was performed by using the semi dry electrophoretic transfer unit PhastTransfer™ (Pharmacia, Sweden) according to the manufacturer's instructions. Proteins from gels after SDS-PAGE were electrophoretically transferred onto nitrocellulose membranes. The membranes were then incubated with the rabbit-anti the algal lyase serum (1:100) overnight at room temperature, followed by incubation with the secondary antibodies goat-anti rabbit IgG conjugated to horse-radish peroxidase (1:1000). Lyase band was visualized using 4-chloro-1-naphthol and peroxide as substrates to the peroxidase.

Amino acid composition analysis of =-1,4-glucan lyase

Amino acid analysis was performed on a LKB Model 4151 amino acid analyzer. Norleucine was used as an internal standard. The enzyme samples were hydrolyzed in sealed, evacuated tubes with 6N HCl for 24 and 72 h. Cysteine and methionine contents were determined as cysteic and methionine sulfone, respectively, after performic acid oxidation according to the procedure of Moore, S. ((1963) J. Biol. Chem. 238, 235–237). Protein was determined according to the Bradford method modified by Peterson, G. L. ((1983) Methods Enzymol. 91, 95–119), and BSA was used as a standard.

Partial amino acid sequence analysis

The red algal lyase was dissolved in 60 µl 6M guanidine chloride. To 20 µl of this sample were added 40 µl 0.2M Tris-HCl (pH 8.2) and 1 µl proteinase I from *Achromobacter lyticus* (specific for Lys-X, Wako Pure Chemical Industries LTD, Osaka, Japan). Digestion was carried out at 37° C. overnight. Reduction of the polypeptides produced was performed at 56° C. for 15 min in the presence of 0.1% of 2-mercaptoethanol. The polypeptides were further derivatized using 0.3% of 4-vinylpyridine in the dark for 30 min at room temperature and then separated on HPLC (conditions: buffer A, H$_2$O: TFA=100:0.1; buffer b, acetonitrile:H$_2$O:TFA=90:10:0.1). The polypeptide peaks were monitored at 214 nm, collected, and stored at −20° C. before being applied onto a gas-phase sequencer (Applied Biosystem, model 470A) equipped with an online HPLC detection system.

Purification of α-1,4-glucan lyase and production of antibodies

The purified enzyme 1.2 mg in 370 µl 0.85% NaCl and 0.1% NaN$_3$ was used as an antigen. Immunization of rabbits was carried out by DAKO A/S (Denmark) according to the procedure detailed by Harboe and Ingild (Scand. J. Immunol. 17, Suppl. 10, 345–351, 1983).

We claim:

1. An isolated and purified exo-α-1,4-glucan lyase enzyme selected from the group consisting of α-1,4-glucan lyase isolated from an alga and its enzymatically active mutants.

2. An enzyme according to claim 1, wherein said alga is a red seaweed of the order Gigartinales.

3. An enzyme according to claim 2, wherein said red seaweed is chosen from the group consisting of *Gracilariopsis lemaneiformis*, *Gracilaria verrucosa* and *Phyllophora truncata*.

4. An enzyme according to claim 1, wherein said enzyme is in immobilized form.

5. An enzyme according to claim 1, wherein said enzyme has an amino acid sequence which comprises at least one of the following fragments with amino acid sequence of: Fragment 1 (SEQ ID NO: 1), Fragment 2 (SEQ ID NO: 2), Fragment 3 (SEQ ID NO: 3) or Fragment 4 (SEQ ID NO. 4).

6. An enzyme according to claim 1, wherein said enzyme has an isoelectric point of around 3.9 and an approximate molecular weight of 111,000 Da by SDS-gel electrophoresis and 98,000 Da by gel filtration chromatography and the following amino acid composition determined as amino acid residues per molecule by amino acid analysis:

Asx 155, Thr 71, Ser 57, Gly 94, Pro 49, Gly 98, Ala 52, Cys 15, Val 70, Met 21, Ile 41, Leu 61, Tyr 62, Phe 52, His 16, Lys 37, Arg 48, and Trp not determined.

7. An enzyme according to claim 1, wherein said enzyme has a molecular weight of about 54,000 Da.

8. A method of cleaving the terminal α-1,4-D-glucosidic bonds from the non-reducing ends of an α-1,4-glucan, characterized in that said α-1,4-glucan is brought into contact with an enzyme according to claim 1.

9. A method according to claim 8 where said α-1,4-glucan comprises branched chains and said enzyme is used together with a polysaccharide debranching enzyme.

10. A method according to claim 8, wherein the degradation product comprises 1,5-anhydrofructose.

11. A method of producing the enzyme of claim 1 capable of successively cleaving the terminal α-1,4-D-glucosidic bonds from the non-reducing ends of an α-1,4-glucan, characterized in that it is isolated from an alga by extraction and purification in per se known manner, or it is produced and purified from a culture of transformed cells with the nucleotide sequence coding for an algol α-1,4-glucan lyase.

12. A method according to claim 9, wherein the polysaccharide debranching enzyme is pullulanase.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 21 amino acids
( B ) TYPE: amino acid
( D ) TOPOLOGY: linear ( i i ) MOLECULE TYPE: protein ( i i i ) HYPOTHETICAL: NO ( v ) FRAGMENT TYPE: internal ( v i ) ORIGINAL SOURCE:
( A ) ORGANISM: Gracilariopsis lemaneiformis/Gracilaria verrucosa ( i x ) FEATURE:
( A ) NAME/KEY: Modified-site
( B ) LOCATION: 1
( D ) OTHER INFORMATION: /label=SEQIDNO1
/ note= "Xaa in position 1 is Tyr or Val"

( i x ) FEATURE:
( A ) NAME/KEY: Modified-site
( B ) LOCATION: 4
( D ) OTHER INFORMATION: /label=SEQIDNO1
/ note= "Xaa in position 4 is Pro or Thr"

( x i ) SEQUENCE DESCRIPTION: SEQ ID NO: 1:

```
Xaa  Met  Val  Xaa  Asn  Met  Tyr  Tyr  Glu  Asn  His
 1                 5                          10

Gly  Tyr  Glu  Pro  Met  Val  Thr  Gln  Tyr  Asn
             15                          20
```

( 2 ) INFORMATION FOR SEQ ID NO: 2:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: Gracilariopsis lemaneiformis/Gracilaria
            verrucosa ( x i ) SEQUENCE DESCRIPTION: SEQ ID NO: 2:

```
Gly Leu Val Pro Gln Thr Asp Ile Thr Pro Phe Leu
 1               5                   10

Arg Asp Asn Asp Glu Gly Gln Asn Tyr Glu Val Asn
             15                  20

Gln Thr Leu Arg Glu Arg
 25              30
```

( 2 ) INFORMATION FOR SEQ ID NO: 3:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: Gracilariopsis lemaneiformis/Gracilaria
            verrucosa ( i x ) FEATURE:
        ( A ) NAME/KEY: Modified-site
        ( B ) LOCATION: 1
        ( D ) OTHER INFORMATION: /label=SEQIDNO3
           / note= "Xaa in position 1 is Gly or Val"

( x i ) SEQUENCE DESCRIPTION: SEQ ID NO: 3:

```
Xaa Ala Ala Glu Gln Asn Gly Gly Thr Glu Thr
 1               5                   10

Ile Thr Phe Thr Asp Asn Pro Tyr Arg Tyr Val Phe
             15                  20

Gly Gly
 25
```

( 2 ) INFORMATION FOR SEQ ID NO: 4:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: internal ( v i ) ORIGINAL SOURCE:

(A) ORGANISM: Gracilariopsis lemaneiformis/Gracilaria verrucosa (ix) FEATURE:
   (A) NAME/KEY: Modified-site
   (B) LOCATION: 1
   (D) OTHER INFORMATION: /label=SEQIDNO4
      / note= "Xaa in position 1 is Gly or Ser"

(ix) FEATURE:
   (A) NAME/KEY: Modified-site
   (B) LOCATION: 4
   (D) OTHER INFORMATION: /label=SEQIDNO4
      / note= "Xaa in position 4 is Thr or Leu"

(ix) FEATURE:
   (A) NAME/KEY: Modified-site
   (B) LOCATION: 9
   (D) OTHER INFORMATION: /label=SEQIDNO4
      / note= "Xaa in position 9 is Phe or Asp"

(ix) FEATURE:
   (A) NAME/KEY: Modified-site
   (B) LOCATION: 24
   (D) OTHER INFORMATION: /label=SEQIDNO4
      / note= "Xaa in position 24 is Asp or Leu"

(xi) SEQUENCE DESCRIPTION: SEQ ID NO: 4:

```
Xaa  Leu  Asn  Xaa  Tyr  Thr  Asp  Glu  Xaa
 1                   5

Pro  Leu  Val  Phe  Glu  Val  Phe  Pro  Leu  Gly  Asn  Asn
10                       15                      20

Arg  Ala  Xaa  Gly
              24
```